US012766028B2

(12) United States Patent
Goode et al.

(10) Patent No.: US 12,766,028 B2
(45) Date of Patent: Oct. 20, 2026

(54) PERSONALIZED DEVICE BASEPLATE USING 3D SCANNING AND SUBSTRACTIVE MANUFACTURING

(71) Applicant: Carilion Clinic, Roanoke, VA (US)

(72) Inventors: Adam Goode, Roanoke, VA (US); Christopher Arena, Blacksburg, VA (US); Robert Fippinger, Roanoke, VA (US)

(73) Assignee: Carilion Clinic, Roanoke, VA (US)

( * ) Notice: Subject to any disclaimer, the term of this patent is extended or adjusted under 35 U.S.C. 154(b) by 402 days.

(21) Appl. No.: 18/385,860

(22) Filed: Oct. 31, 2023

(65) Prior Publication Data

US 2024/0139022 A1 May 2, 2024

Related U.S. Application Data

(60) Provisional application No. 63/420,907, filed on Oct. 31, 2022.

(51) Int. Cl.
*A61F 5/445* (2006.01)
*G05B 19/4099* (2006.01)
*A61F 5/448* (2006.01)

(52) U.S. Cl.
CPC .......... *A61F 5/445* (2013.01); *G05B 19/4099* (2013.01); *A61F 2005/4483* (2013.01); *G05B 2219/35134* (2013.01)

(58) Field of Classification Search
CPC .......................................................... A61F 5/44
See application file for complete search history.

(56) References Cited

U.S. PATENT DOCUMENTS 6,659,989 B1 * 12/2003 Otto ........................ A61F 5/445 604/339
2024/0315865 A1 * 9/2024 Wines ..................... A61F 5/443
2024/0398606 A1 * 12/2024 Czaplewski ........... B33Y 50/00

FOREIGN PATENT DOCUMENTS

WO 2017106911 A1 6/2017

* cited by examiner

*Primary Examiner* — Paul B Yanchus, III
(74) *Attorney, Agent, or Firm* — Woods Rogers Vandeventer Black PLC; Nathan A. Evans

(57) ABSTRACT

A personalized ostomy appliance, including a baseplate, leveraging three-dimensional ("3D") scanning, computer-aided design modeling, and 3D printing technology, to empower patients to improve quality of life and decrease ostomy complications. In embodiments, the process uses 3D scanning technology to create a raw peristomal mesh. In embodiments, this mesh is filtered using a smoothing and splicing algorithm with patient-specified preference variables. In embodiments, this personalized filtered mesh is then used in a subtractive manufacturing process, including applying a laser cutter or blade press, to alter an ostomy baseplate. The personalized filtered mesh can also used to 3D print a personalized ostomy template that improves fit of the baseplate using a retraction method. This process can be applied to wound care with negative pressure vacuum therapy and fistula management systems wherein a vacuum or pouch baseplate is generated for improved fit and healing.

16 Claims, 17 Drawing Sheets

PERSONALIZED DEVICE BASEPLATE USING 3D SCANNING AND SUBSTRACTIVE MANUFACTURING

CROSS-REFERENCE TO RELATED APPLICATION

The present application relies on the disclosures of and claims priority to and the benefit of the filing date of the following U.S. Patent Application 63/420,907, filed Oct. 31, 2022. The disclosures of that application are hereby incorporated by reference herein in their entireties.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD OF INVENTION

The present invention relates generally to an ostomy connection device and connection system and more specifically to a system and method for creating and securing a personalized ostomy device to a patient.

BACKGROUND

An ostomy is a connection between a hollow organ and skin, for example, a colostomy (colon and skin) or an ileostomy (small bowel and skin). These connections are sometimes permanent, e.g., status-post abdominal-perineal resection for low rectal cancer or a total proctocolectomy for refractory inflammatory bowel disease, or temporary, e.g., fecal diversion after sigmoidectomy for complicated diverticulitis or after resection of a distal rectal cancer to protect a high-risk colorectal anastomosis. According to UpToDate™, “nearly half of all stomas become problematic due to pouching and peristomal skin issues.” The most common ostomy complication is peristomal skin breakdown, varying from dermatitis and superficial ulceration to necrotizing soft tissue infections requiring serial debridements and ostomy re-siting. Skin breakdown is a result of effluent leakage and frequent pouch appliance changes. Other complications include peristomal hernias, prolapse, and high-output effluent.

The currently available ostomy appliances or pouching systems comprise an adhesive baseplate and an attachable, odor-controlling collecting bag. Notably, the same products are used for colostomies and ileostomies, even though they have significant differences in needs and complications. Furthermore, available products are not designed for the variety of body habituses and anatomic locations.

There are several companies manufacturing pouching systems on the market today. Fundamentally, they lack the degree of personalization and accessibility provided by the detailed invention.

The dominant market players, Hollister® and Coloplast®, have advanced adhesive technologies that provide a standard square or circular baseplate. The opening in the baseplate is altered by the patient or caregiver using scissors. The baseplate then attaches to a collecting bag. SenSura Mio® created a convex and concave baseplate to attempt a better fit for protruding or retracted ostomies. This binary choice is then fit using scissors to cut out the stoma opening. Importantly, there is a lack of substantial customization of the device to a given patient.

Therefore, a newly proposed technical solution, as disclosed herein, is the use of three-dimensional (“3D”) scanning, computer-aided design modeling, 3D manufacturing technology, and/or subtractive manufacturing, to customize an ostomy baseplate, in aspects, by improving upon existing products.

BRIEF DESCRIPTION

The present invention is a method and system directed at providing a customizable ostomy collecting system that meets each patient’s unique characteristics and demands. In embodiments, the invention has primarily three components: First, creation of a 3D unfiltered mesh model of the patient ostomy and peristomal skin using a 3D scanning device; Second, filtering of the mesh model to optimize fit according to patient-specified variables; and Third, applying subtractive manufacturing techniques, including but not limited to a laser cutter and blade press, to modify an ostomy baseplate to provide a personalized ostomy appliance. Fourth, a 3D printed ostomy template can be used improve this personalized baseplate further by utilizing a retraction method. In other embodiments, the invention includes scanning a patient’s anatomy, such as the patient’s ostomy and peristomal skin, using a scanning device, and then cutting (e.g., laser cutting) an existing, off-the-shelf ostomy baseplate to provide a custom fit for the patient based on the results of the scan(s).

In embodiments, the first process utilizes a 3D image acquisition device to create a raw contour map of the patient’s stoma and peristomal skin. Such a 3D image acquisition device includes but is not limited to a 3D scanner, a computer with camera, a smart phone with camera, or any other device that could 3D scan a patient’s anatomy, such as the patient’s ostomy and peristomal skin, as would be understood by one of ordinary skill in the art. A second process filters this raw 3D scan mesh model to create a virtual functional baseplate. A third process leverages subtractive manufacturing to create a personalized ostomy baseplate. This personalized ostomy baseplate is further customized via a retraction method as described using a 3D printed ostomy template. This template is able to improve existing baseplates by allowing the patient to mold the baseplate opening to the patient (“Retraction” Method). In other words, based on the 3D scan of the patient’s anatomy, a user can provide an existing baseplate, which can be automatically subtracted from (e.g., using laser ablation) to provide a custom-shaped baseplate for the wearer that improves safety and efficacy of the existing ostomy appliance.

These processes also work for wound and fistula care. For example, a complex wound requiring negative pressure wound therapy is scanned. This unfiltered model is then filtered to create a 3D printed wound template and subtraction method applied to a wound insert, such as a foam wound insert, to provide improved seal and wound bed coverage. Similarly, an enterocutaneous or enteroatmospheric fistula can be better controlled by 3D scanning the wound, followed by filtering this unfiltered mesh, and then providing a wound/fistula template to the patient/wound nurses/medical provider and customized fistula management system (e.g., Eakin’s ring) using the aforementioned subtractive manufacturing method, e.g., laser cutter or blade press.

Further, the present method and system includes multiple varying embodiments. These embodiments can operate independent of each other or can be in combination with one or more other embodiments. In an embodiment, the invention includes acquisition of a raw patient peristomal contour map. Another embodiment includes filtering of a peristomal contour map using one or more data filtering and processing operations. Another embodiment includes printing of the filtered contour map. In another embodiment, an aspect of the invention provides for 3D scanning the patient's anatomy and subtracting material (e.g., using a laser cutter or blade) from an existing ostomy appliance that creates a custom-fitting device for the patient.

Further regarding embodiments, the invention includes the application of a stoma template to alter existing ostomy device baseplates using a cutting material application. Moreover, embodiments include application of a stoma template to alter existing ostomy device baseplates using a retraction method, such as application of stoma template to alter existing ostomy device baseplates using a laser substruction method, or to manufacture an entire customized baseplate using a 3D printing and the laser subtraction method.

Another embodiment includes an incorporation of non-adherent and moisture controlling substances to a baseplate.

In other embodiments, the invention comprises wound care applications, such as 3D scanning, CAD modeling, subtractive manufacturing, and 3D printing wound care treatment(s), that include but are not limited to enterocutaneous/atmospheric fistulas, to assist in fitting negative pressure wound vacuum therapy appliances and/or fistula pouching appliances.

The invention described herein provides a mechanism to create a personalized pouching system to improve patient experience. The present invention can personalize/customize the pouching system to the patient thereby improving fit, decreasing leakage, and improving overall patient experience for each patient's unique needs.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

DETAILED DESCRIPTION

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

Figure 1:
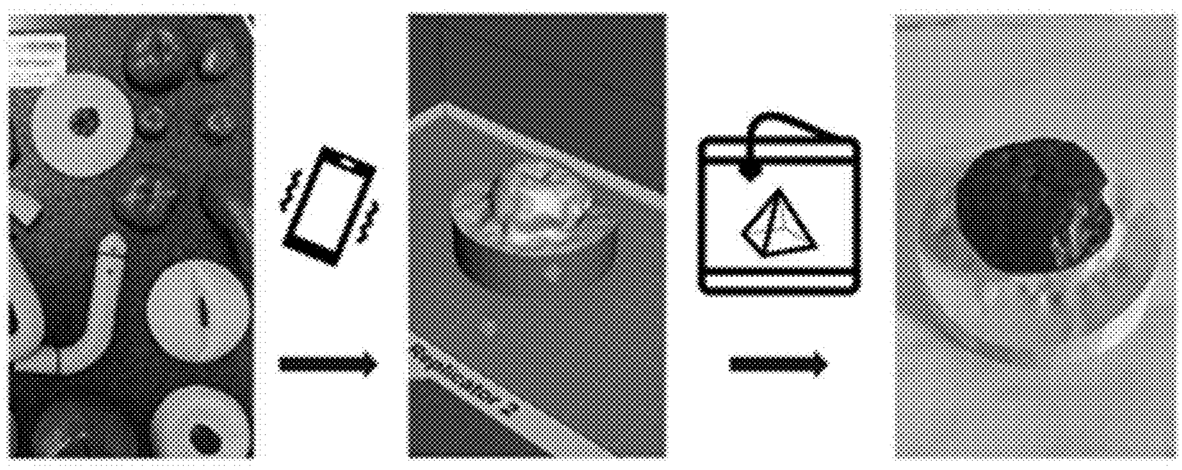
FIG. 1 illustrates a workflow from scanning various stoma models to filtering of raw mesh to 3D printing according to an embodiment of the current invention.

FIG. 1 illustrates a workflow from scanning various stoma models, to filtering of raw mesh to a 3D printed device. In an embodiment, the PolyCam™ app was used on a cell phone to capture multiple images of the stoma simulator and reconstruct a 3D mesh. (Other smart phone or computer-implemented scanning techniques can be used as would be understood by one of ordinary skill in the art.) Herein, the present workflow may utilize any suitable image capture and 3D image reconstruction. The 3D mesh was processed on the computer for 3D printing. This included cutting planes to remove unwanted sections and adding a cylindrical base.

The filtered mesh was then 3D printed creating an ostomy template. The 3D printing may be performed using suitable 3D printing techniques and processing operations as recognized by a skilled artisan.

Figure 2:
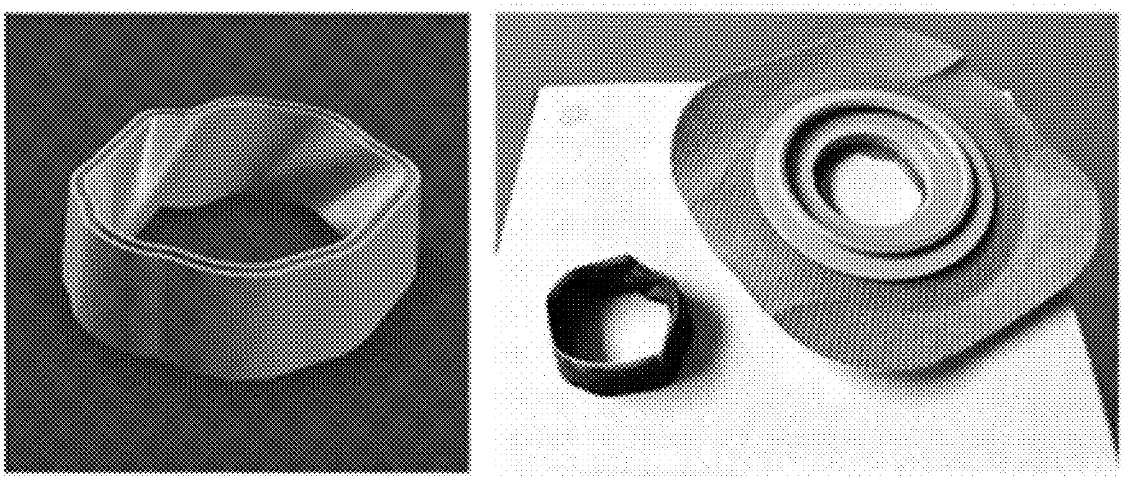
FIG. 2 illustrates a workflow from simulation model of stoma (e.g., patient) to a custom cutter tool according to an embodiment of the current invention.

FIG. 2 illustrates a workflow from a simulation model of an ostomy to custom cutter tool. In an embodiment, the PolyCam™ app was used on a cell phone to capture multiple images of the stoma simulator and reconstruct a 3D mesh model. The 3D model was processed on a computer (e.g., using a computer processor) for 3D printing. In this embodiment, the processing includes using a computer-aided design ("CAD") program to outline the contour of interest around the stoma with various design functions including but not limited to spline, extrude, and/or intersection functionalities, to create the desired mucocutaneous junction circumference. This filtered path was then 3D printed using 3D printing techniques recognized by a skilled artisan. In aspects, a stainless-steel foil blade can be implanted into the custom insert to alter an ostomy baseplate.

Figure 3:
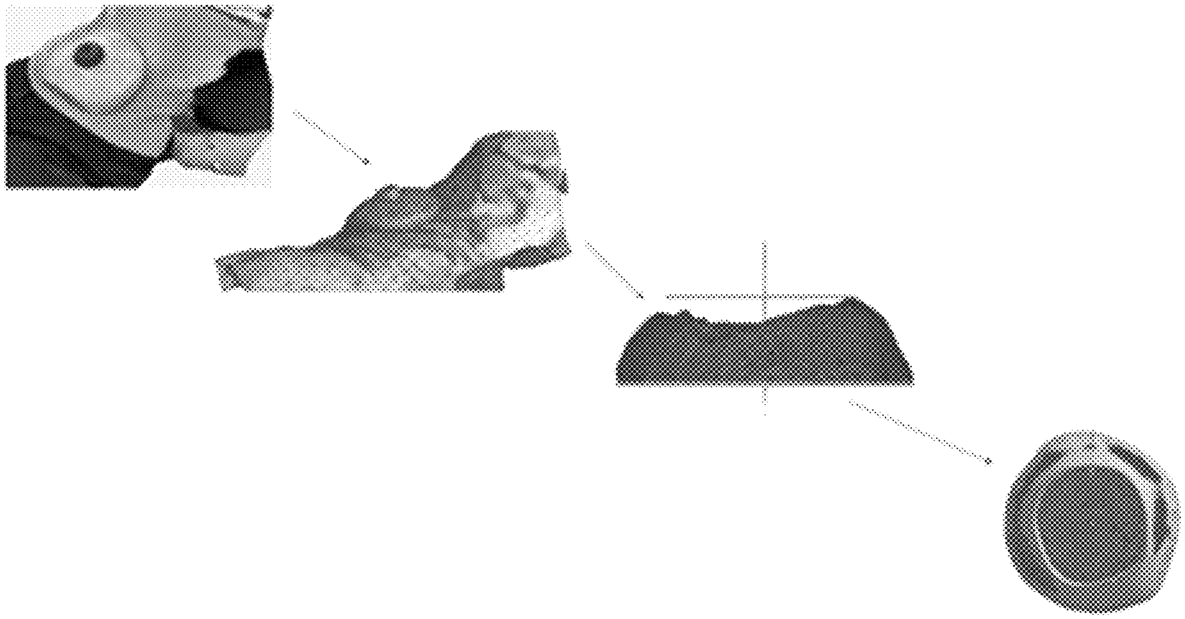
FIG. 3 illustrates a workflow of a process of scanning an ostomy and filtering the raw mesh to create a personalized ostomy template according to an embodiment of the current invention.

FIG. 3 illustrates a workflow showing a process of 3D scanning an ostomy and filtering the raw mesh to create a personalized ostomy template. In an embodiment, a patient goes into, for example, a clinic for their post-op checkup with their physician or other medical provider; in that meeting the ostomy is scanned and sent out for development. In other aspects, the patient, physician, or other medical provider, can scan the anatomy using a 3D scanning mechanism, a smart phone having a camera for 3D scanning, a computer-implemented device for 3D scanning, or any other mechanism for 3D scanning a patient's anatomy as would be understood by one of ordinary skill in the art. Using CAD software in this example, an .stl file can be imported and outlined on a plane that corresponds with the bottom and top of the ostomy. From there, a loft and thicken feature can be used to connect the sketches and partially or, preferably, completely enclose the ostomy.

In aspects, patient-specified variables, such as degree of retraction or protrusion, peristomal wounds, and/or peristomal abdominal wall creases, are then added to further customize the mesh, such as 3D printing an ostomy appliance or subtracting from an existing ostomy appliance to improve fit of the existing ostomy appliance for the particular patient based on the patient's anatomy, ostomy, or other features specific to that patient. The final product is a unique template for the ostomy. It is understood this procedure can be used for both protruded and retracted ostomies.

In aspects, patient-specific variables relate to alterations in the filtered mesh contour based upon patient and provider feedback. These variables include, but are not limited to, (1) skin coverage offset—the radial edge offset between the mucocutaneus border, (2) ostomy height coverage—the excess height of the ostomy that will not be covered, (3) ostomy grade—the baseplate slope from the maximum height to the peristomal skin surface height, and (4) inclusion/exclusion zones—areas on the peristomal skin, e.g., open wound, that should be altered with additional baseplate coverage or potentially excluded to allow for a specialized dressing to be inserted. This may be particularly useful in the case where the peristomal skin is ulcerated. The personalized ostomy mesh or ostomy appliance can be altered according to these patient-specified variables.

Figure 4:
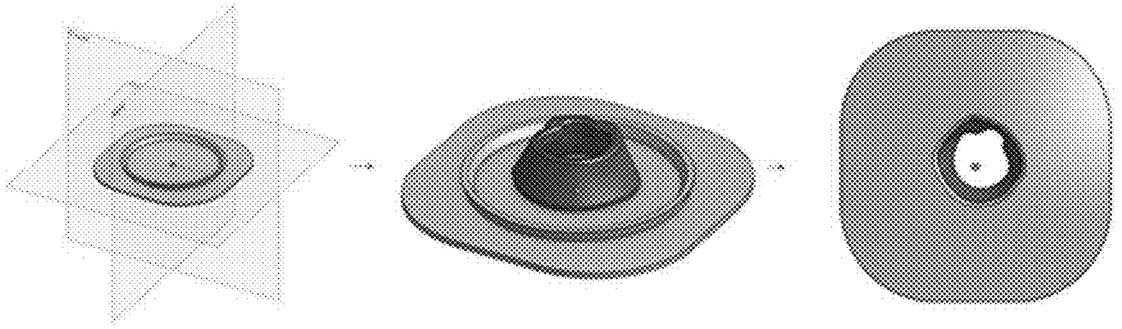
FIG. 4 illustrates a workflow of a progression of using the 3D mesh file of the stoma mold and combining it with a model of a current commercially used baseplate for stoma care, according to an embodiment of the current invention.

FIG. 4 illustrates a workflow showing a progression of using the 3D mesh file (or other model) of the ostomy mold and combining it with a model of a current existing, commercially-available baseplate for ostomy care. In embodiments, first the baseplate is oriented, and the 3D mesh file is imported into the same assembly, from there the bottom of the custom ostomy mold and the top of the baseplate are mated together. Then the geometry of the stoma mold is cut out of the existing baseplate to generate a unique stoma care unit. This 3D file can then be exported and printed via any 3D printer capable of printing a flexible, biocompatible material. Once printed, adhesive can be added to the back of the baseplate to secure it during use, and once that is done the product can be ready for patient use. Since the baseplate utilizes similar geometry from commercially used ostomy collecting systems ("bag"), the same bag can be used with this product.

Figure 5:
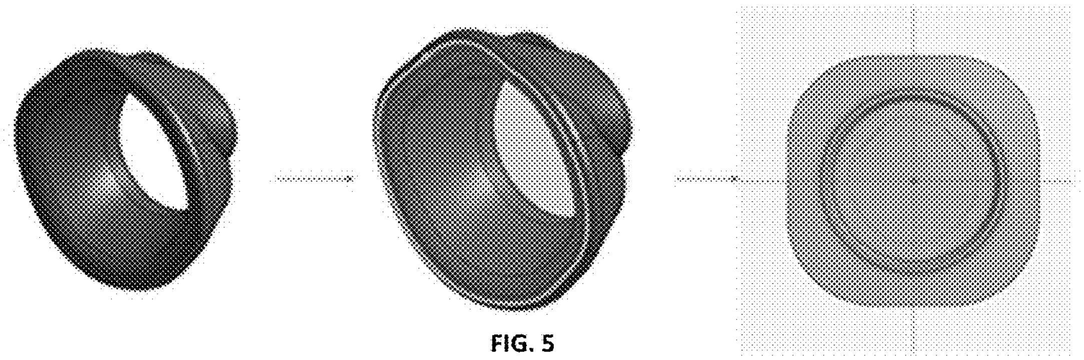
FIG. 5 illustrates a workflow of a progression from 3D scan to custom laser cut baseplate according to an embodiment of the current invention.

FIG. 5 illustrates a workflow showing the progression from 3D scan to custom laser cut baseplate. Using a scan from the patient's stoma, a 3D mesh or similar 3D model reconstruction can be generated. In aspects, a tracing tool in CAD can be used to trace the outline of the base of the stoma, which can then be translated to a .jpg or .dxf file, by way of example, and used to cut out on a laser cutter. This can provide for an exact, nearly exact, mostly exact, or substantially exact, fit around the base of the ostomy, eliminating exposed skin around the stoma. In embodiments, this process can be implemented with current commercially available 2-part baseplates since they are made of a hydrocolloid materials, which are compatible with using a laser to cut the material.

Figure 6:
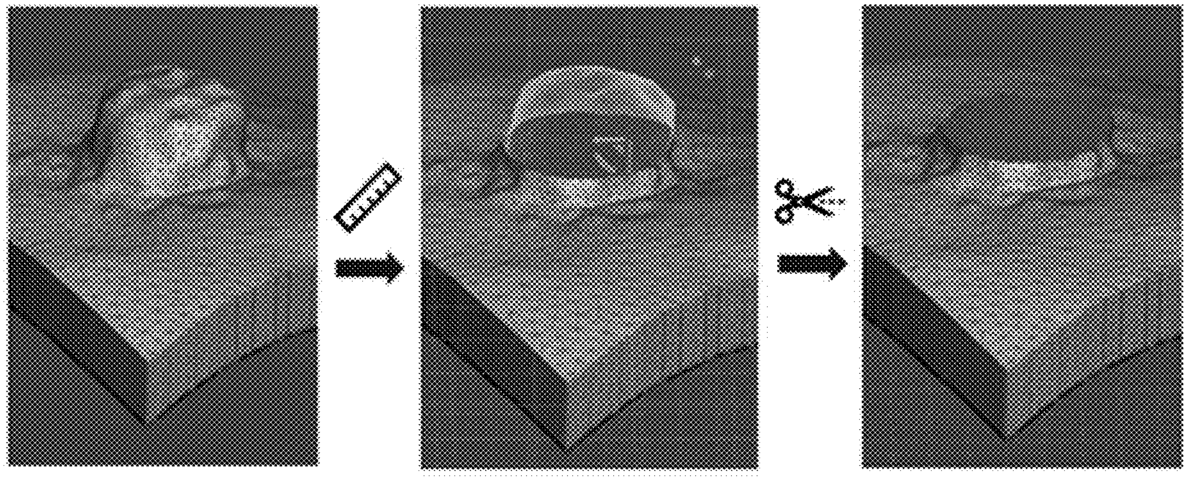
FIG. 6 illustrates a workflow for processing a 3D scan based on patient preference variables according to an embodiment of the current invention.

FIG. 6 illustrates a workflow for processing a 3D scan based on patient preference variables. For example, the location of the cutting plane, which forms the basis for the device contour, can be selected based on the protrusion of the stoma (e.g., around 1 cm). Patient preference variables can be input manually, automatically, or optimized based on an algorithm (e.g., maximize skin coverage but minimize ostomy coverage).

Figure 7:
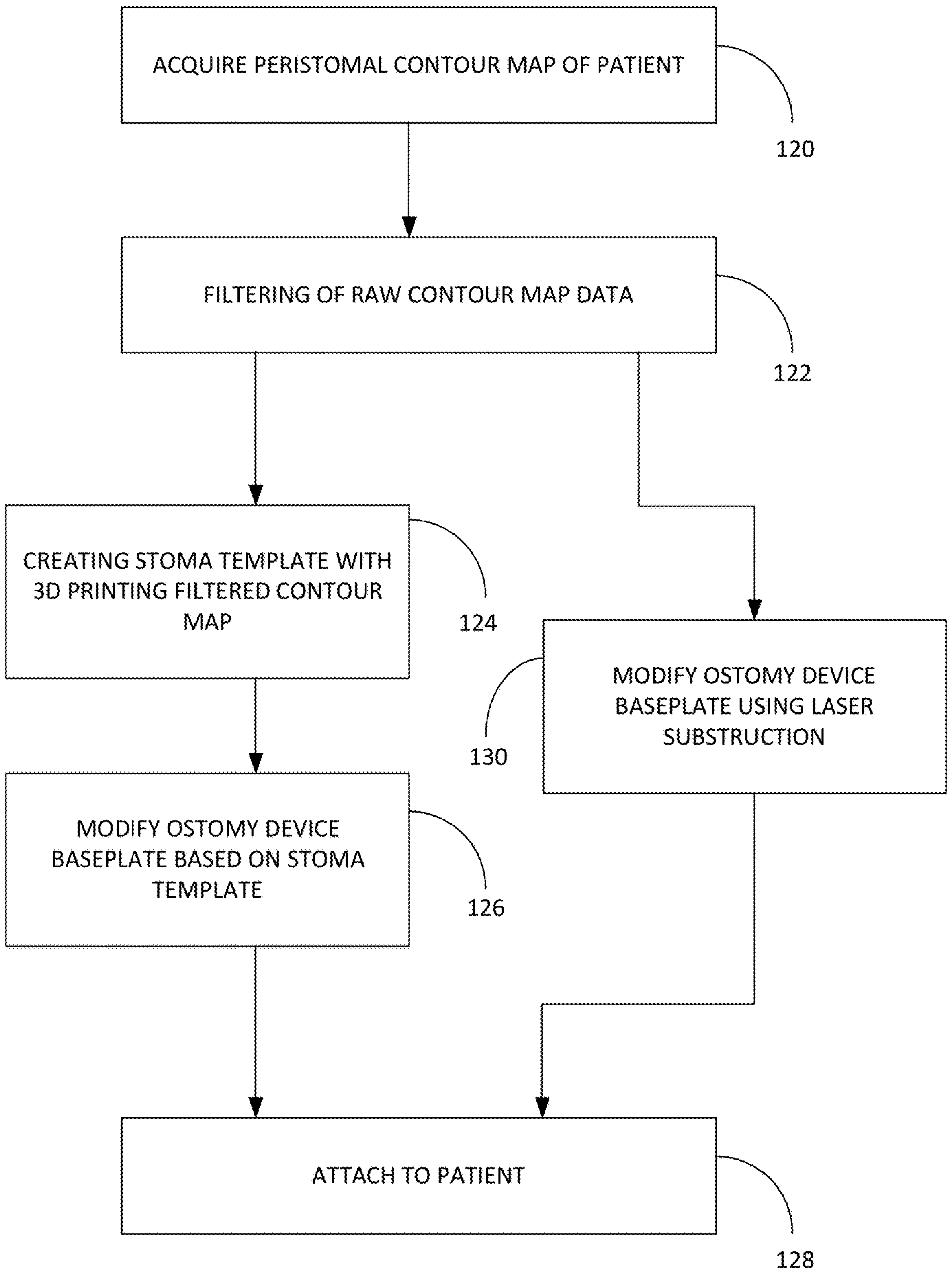
FIG. 7 illustrates a flowchart of one embodiment of a methodology of the present invention.

FIG. 7 illustrates varying embodiments of methods according to the present invention. Step 120 is acquiring a peristomal contour map of the patient, for example as noted in FIG. 1 or 2 above. Step 122 is filtering raw contour map data, for example consistent with techniques noted above including but not limited to FIG. 3 above.

In embodiments, step 124 is creating a stoma template with one or more 3D printing filtered contour map. Therewith, step 126 is modifying an existing ostomy device baseplate based on the stoma template of step 124. These steps can be performed consistent with, for example, FIG. 4 above.

Step 128 is attaching the modified ostomy device baseplate to the patient. This step can be performed by the patient, a physician, a technician, a medical provider, or a medical assistant using known techniques, wherein the modified ostomy device baseplate is improved and provides additional benefits noted herein. This step, in aspects, can also be performed by the patient.

In embodiments, the method may include step 130 of modifying the existing ostomy device baseplate using laser substruction. This step may be in alternative to steps 124 and 126, for example. Thereupon, the method continues to step 128 for attachment to patient. By way of example, a stoma or relevant anatomy of a patient can be scanned, such as 3D scanned, using a mobile phone with a camera or other scanning technique that would be understood by one of ordinary skill in the art. Based on the scan, the current invention can determine an optimized fit for a baseplate of an existing ostomy appliance, and a customized mesh. Based on the customized mesh, a subtraction technique, such as laser subtraction, can be used to cut or otherwise shape the existing baseplate in order to create a custom-shaped baseplate that will ensure a better fit of the baseplate to the site, such as an ostomy site, to be treated. The scan can be processed to create a three-dimensional mesh around the stoma and surrounding regions of interest. In embodiments, via computer-aided design, a custom contour can be defined by taking the intersection of the outer stoma boundary with a cutting plane at a desired height. The contour can be offset either inward or outward from the intersection boundary to provide all, more, or less, coverage of the stoma, respectively. Alternatively, one could use splines, shape matching, contour matching, or other optimization algorithms to outline the boundary of the stoma. This may be chosen based on maximizing the coverage of the peristomal area. It could also allow for expansion or contraction of the stoma. The computer-generated boundary can then be exported as a scalable vector graphics file and imported into software for laser (or other) cutting. The laser cutting settings can be tuned to either cut the ostomy baseplate fully according to the contour, or engrave the contour for later cutting. One could also cut the custom contour into a paper (or other material) guide and later transfer the shape to the ostomy baseplate through tracing and/or cutting.

In aspects, once the peristomal mesh is obtained, it is then filtered to highlight the interface between the mucocutaneous junction. Using a CAD modeling software system, for example, a plane is intersected at this junction to highlight the circumference. If the ostomy is protruding, a z-axis slightly above the exact mucocutaneous junction circumference can be chosen, for example; whereas, if the ostomy is retracted, an exaggerated radial circumference can be chosen. These variables, the radial exaggeration and z-axis height, by way of example, are able to be adjusted based upon patient feedback from using the personalized ostomy appliance. Next, in aspects, a cylinder extrusion function can be applied to create an ostomy template that features the peristomal skin in addition to the stoma itself. In aspects, abrupt edges can be treated using a smoothing algorithm.

In embodiments, the method and system can include acquisition of one or more raw patient peristomal contour map. In embodiments, a peristomal mapping protocol can be applied that results in a personalized contour map of a patient for purposes of fitting an ostomy device. A variety of technologies can be used to map the area to be treated. By way of example, a three-dimensional scan can be used; alternatively, a two-dimensional scan can be used if the two-dimensional scan or series of photographs can be used to extrapolate a three-dimensional contour map. By way of example, a smartphone infrared camera can be used to map the contour of the stoma and/or surrounding area. A 3D scanner can be used, such as a handheld or other 3D scanner. Other options include a two-lens imaging system, or a physical contour device. In embodiments, the individual stoma mapping can be uploaded into a CAD file (or other relevant format) that would allow for three-dimensional printing, additive manufacturing, and/or subtractive manufacturing of, for example, an adhesive ostomy baseplate (or template that would be used to shape, make, or cut the baseplate).

In embodiments, the method and system include printing of one or more filtered contour maps. The filtered and personalized contour map can be printed using existing 3D printing technology. This includes, but is not limited to, fused deposition modeling, stereolithography, and selective laser sintering. Post-processing techniques can also be applied to smooth the surface of the print, such as vapor smoothing. Other manufacturing techniques can also be applied to fabricate the ostomy model. This includes machining or 3D printing a mold and using injection molding or vacuum forming to create the device.

Figure 8:
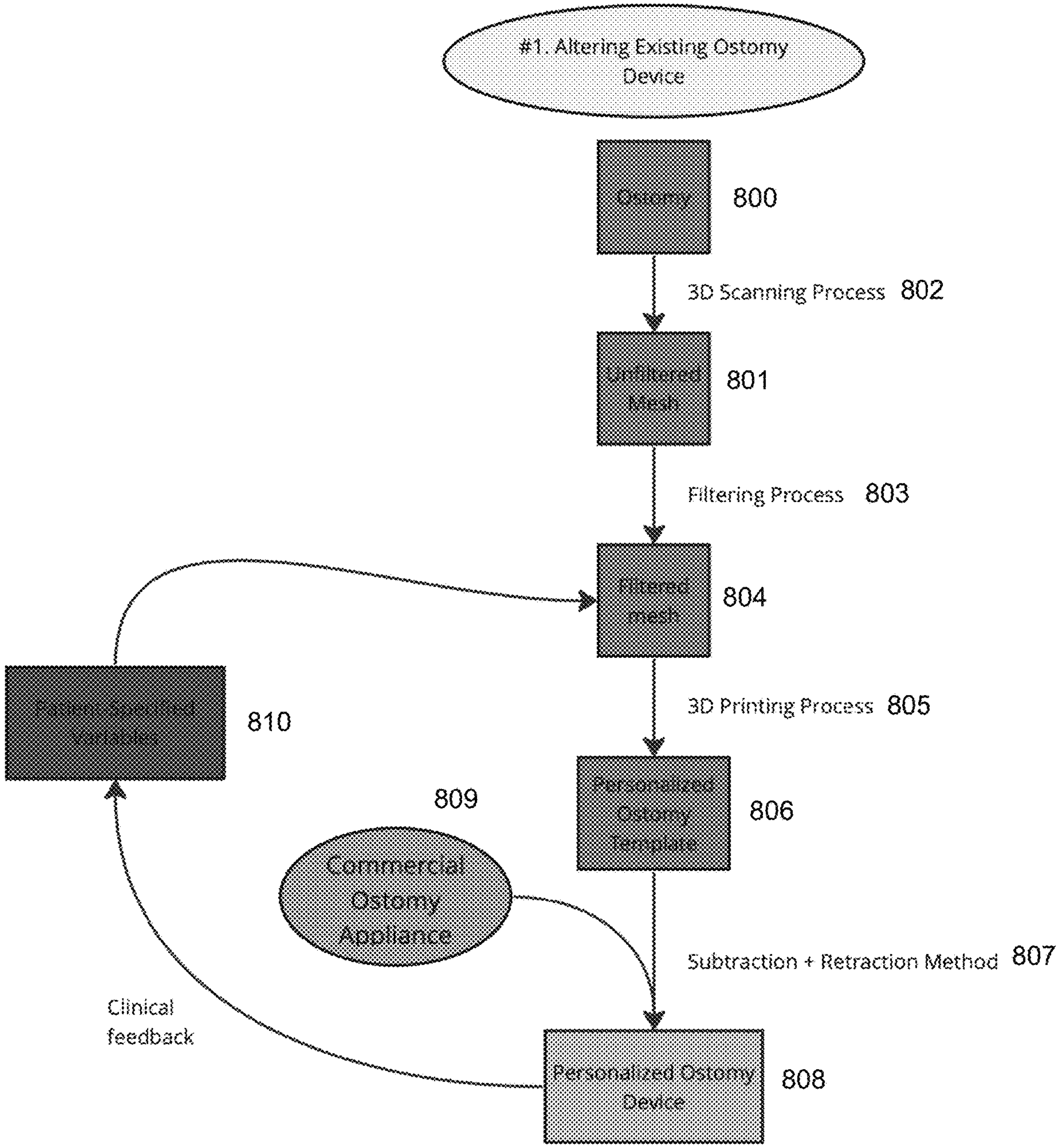
FIG. 8 illustrates a flowchart of creating a personalized ostomy device using an existing, commercially available device by applying the "Retraction" and "Subtraction" methods with the personalized ostomy template.
Figure 9:
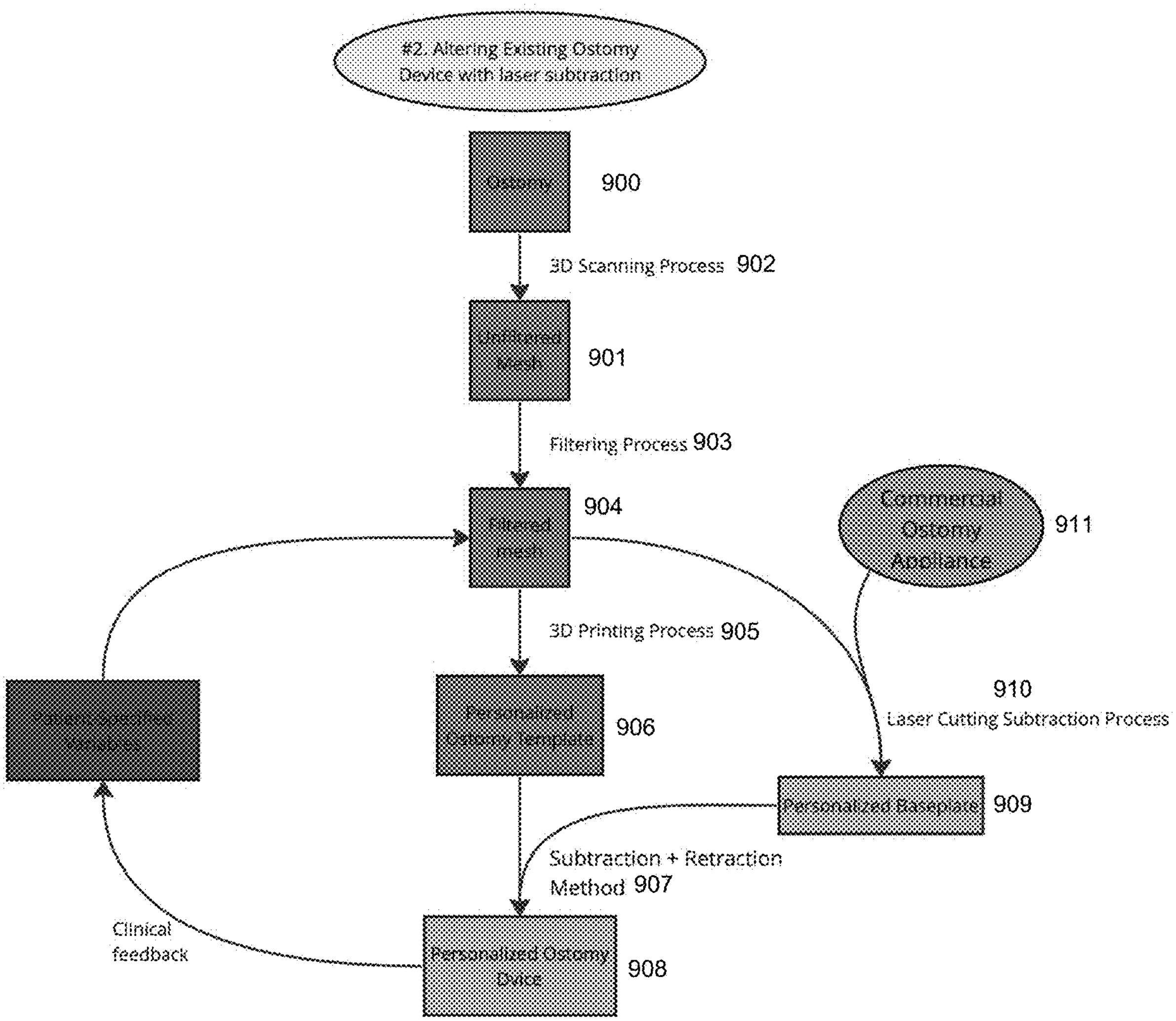
FIG. 9 illustrates a flowchart of creating a personalized ostomy device by altering an existing, commercially available device using the "Laser Subtraction" method and by applying the "Retraction" and "Subtraction" methods with the personalized ostomy template to this altered baseplate.
Figure 10:
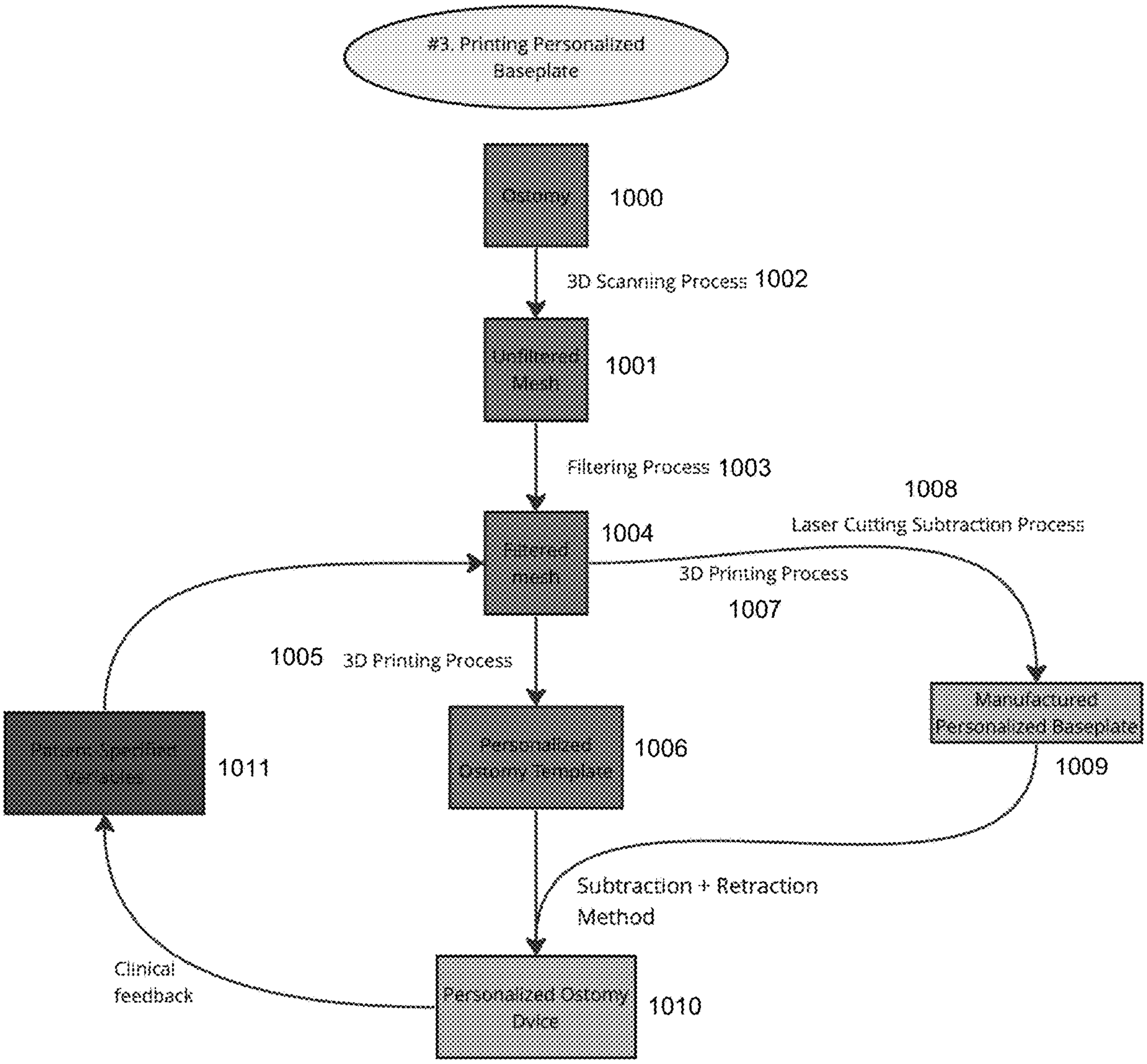
FIG. 10 illustrates a flowchart of creating a personalized ostomy device by manufacturing a functional baseplate using the "Laser Subtraction" method and by applying the "Retraction" and "Subtraction" methods with the personalized ostomy template to this baseplate.

FIGS. 8-10 illustrate a process according to the present invention of creating a personalized ostomy device. In FIG. 8, for example, a commercially-available ostomy device is applied by using a personalized template with the application of the "Retraction" and "Subtraction" methods. FIG. 9 shows an embodiment wherein a commercially-available ostomy device is altered using the "Laser Subtraction" method, by applying the personalized ostomy template to fit the baseplate, and the baseplate is formed by cutting away material from the baseplate based on the customized template. That process results in a customized baseplate—from the existing non-customized appliance baseplate—which will better fit the patient according to the 3D scan. Similarly, in FIG. 10, a functional and personalized baseplate is manufactured using the personalized ostomy template to create a personalized baseplate for the patient based on the 3D scan(s). In other words, a customized template is created, the template is used to subtract and/or retract material from an existing ostomy appliance baseplate, and the process results in a customized baseplate tailored to the specific patient.

In embodiments, the method and system can include application of one or more stoma templates to alter an ostomy device baseplate using a cutting material (e.g., "cookie-cutter") application herein described as the "Subtraction" Method. The altered baseplate can then be molded around the ostomy template herein described as the "Retraction" Method. These two methods will be referred to as Step 807. (See, e.g., FIG. 8.) For example, as shown in FIG. 8, an ostomy 800 is scanned to create an unfiltered mesh or other model 801 in step 802, the 3D scanning process. A filtering process in step 803 as described herein provides a filtered mesh or model 804, and a 3D printing process in step 805 is used to create a personalized ostomy template 806. A subtraction and/or retraction method can be used in step 807 to create the personalized ostomy device 808, using the personalized ostomy template to alter (via, e.g., subtraction and/or retraction) a customized, commercial ostomy baseplate that is part of an existing commercially-available ostomy appliance 809, by way of example. In aspects, clinical feedback updates, such as patient-specified variables 810, as described herein, which inform the filtered mesh/model, can provide a feedback loop that informs the filtered mesh/model, improves the filtered mesh, helps create the filtered mesh/model, helps create future filtered meshes, helps create customized template(s), improves patient treatment, improves efficacy, improves fit, improves safety, and so on.

In embodiments of the current invention, the device can include a cutting blade embedded in (or otherwise included with) the template to enable patients to shape, cut, and/or divide, an existing baseplate material for a more personalized opening and/or fit. The patient could then use the template using the retraction method described below or elsewhere herein to customize a baseplate.

In embodiments, the method and system can include application of one or more stoma template to alter existing ostomy device baseplates using a retraction method. For example, once the personalized ostomy template is created or printed based on the 3D scan, the patient (or other user, such as a medical provider or ostomy maker) can mold (or cut) the ostomy baseplate around the ostomy template. This will approximate the unique shape of the scanned ostomy and the peristomal skin shape.

In embodiments, the method and system include application of one or more stoma template to alter existing ostomy device baseplates using laser subtraction. (See, e.g., FIG. 9.) In aspects, the inventive process could be used to allow patients (or their medical providers) to submit a requested ostomy device and have a laser cut or print out, for example, a peristomal skin edge for the device, instead of the cutting blade method illustrated in e.g., FIG. 4. Using, for example, a top view of the scanned ostomy, it is possible to outline a shape and size of the ostomy and export that image or scan as a .jpeg or .dxf file, by way of example. This custom shape can then be uploaded to, e.g., commercial laser cutters, which can remove excess material from the baseplate. This would then allow the patient or medical provider to proceed with the method detailed above, for example as noted relative to FIG. 4, to create a customized device and/or baseplate, even from existing, off-the-shelf ostomy devices/baseplates.

As shown in FIG. 9, an ostomy 900 can be scanned to create an unfiltered mesh or other model 901 in step 902, the 3D scanning process. A filtering process in step 903 as described herein provides a filtered mesh or model 904, and a printing process (such as a 3D printing process) in step 905 can be used to create a personalized ostomy template 906. A subtraction and/or retraction method can be used in step 907 to create the personalized ostomy device 908. In the embodiment shown in FIG. 9, by way of example, the filtered mesh or model can also be used for a laser cutting subtraction and/or retraction step 910 that creates a personalized baseplate 909 from a commercial ostomy appliance 911. In aspects, clinical feedback teaches patient-specified variables 912, as described herein, which can inform the filtered mesh or model, and a feedback loop can inform the filtered mesh or model, improve the filtered mesh/model, be used to create the filtered mesh/model, be used to create future filtered meshes/models, be used to better treat the patient, and so on. In FIG. 9, the commercial ostomy appliance 911 can first be altered using the laser cutting subtraction and/or retraction process 910 prior to applying the personalized ostomy template 906 to fit a baseplate.

In another embodiment shown, for example, in FIG. 10, the invention can include printing a personalized baseplate, such as 3D printing a personalized baseplate. In this embodiment, an ostomy or related anatomy 1000 is scanned to create an unfiltered mesh or model 1001 in step 1002, the 3D scanning process. A filtering process in step 1003 as described herein can, in aspects, provide a filtered mesh/model 1004, and a printing process (such as a 3D printing process) in step 1005 can be used to create a personalized ostomy template 1006. Using the filtered mesh/model 1004, a personalized ostomy template 1006 can be generated using a printing process 1007 (such as a 3D printing process). Also using the filtered mesh/model, a printing process (such as a 3D printing process) 1007 along with a subtraction and/or retraction method (such as a laser cutting subtraction process) 1008 can be used to manufacture a personalized baseplate 1009 and thereby a personalized ostomy device 1010. In aspects, clinical feedback updates on patient-specified variables 1011, as described herein, can inform the filtered mesh/model and a feedback loop can inform the filtered mesh/model, improve the filtered mesh/model, be used to create the filtered mesh/model, be used to create future filtered meshes/models, be used to better treat the patient, and so on. In FIG. 10, a functional and personalized baseplate can be manufactured prior to applying the personalized ostomy template to fit the personalized baseplate.

In embodiments, the method and system can include a platform for skin health, effluent volume, and effluent consistency measurements. With this personalized baseplate, the platform can allow biometric sensors to measure (1) peristomal skin health with, for example, a light diode using spectroscopy, which would provide preemptive notification for peristomal skin breakdown prior to complications. In aspects, two electrodes in the collecting system (e.g., "bag") that induce an AC current could allow measurement of the effluent impendence at different frequencies, which would allow improved measurement of volume and consistency to better predict a need for anti-motility agents and/or other ostomy effluent altering interventions. These one or more sensors can be embedded into a computer or smart phone application, by way of example, or the devices taught herein. In aspects, the application could integrate with electronic medical record systems or servers, that would alert designated healthcare provider(s) or patient(s) of pre-specified critical levels of output or consistency in an effort to decrease dehydration, readmission, and/or acute/chronic kidney injury. The information could also alert the patient. For example, if the patient reports increased ileostomy output over the course of two weeks at a clinic visit, the surgeon/physician/clinician/treatment provider may increase or otherwise modify a variety of agents including, but not limited to, fiber, loperamide, atropine, and/or even tincture of opium. The computer software application could improve on this current standard of care by, for example: 1) standardizing predictable care; 2) providing feedback to the patient and/or physician; and/or 3) creating a biofeedback algorithm to recommend titrating specific medications (or other treatments) in a physician approved dose-range.

In embodiments, the method and system can include incorporation of non-adherent and/or moisture controlling substances to a baseplate. To prevent peristomal skin breakdown, specialized wound care products can be applied to the printed baseplate. For example, using either additive printing methods or photolithography techniques, the baseplate can be altered to have channels that wick moisture to the periphery. The surface can also be optimized to have moisture absorptive properties to prevent excess moisture on the skin. The surface can also be coated with non-adhesive materials to limit skin breakdown when removing the baseplate from the skin surface. Further, antimicrobial compounds, such as silver, can be conjugated to the baseplate surface.

EXAMPLE

Figure 11:
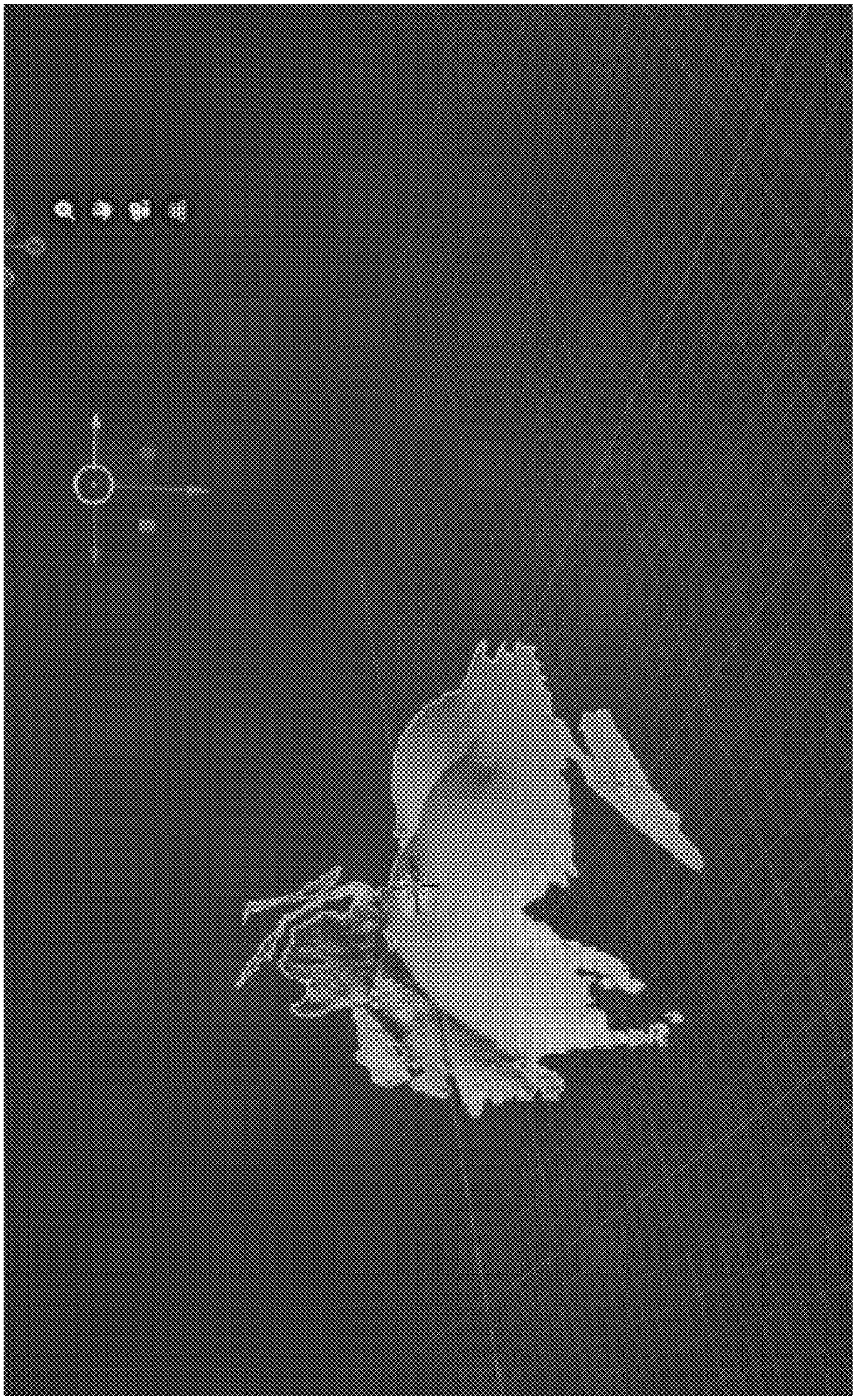
FIG. 11 shows an example of using computer-implemented software to practice aspects of the invention described herein.

FIG. 11 shows an example of using computer-implemented software to practice aspects of the invention described herein. In aspects, a patient or medical provider can manually or automatically acquire a 3D scan of a patient's stoma and/or surrounding area using a handheld 3D scanner or phone application that acquires and processes a series of images. (In aspects, at least one image or combination of images, such as a 3D scan, are used to create a 3D mesh or model.) A mesh manipulation software such as Blender™ or Meshmixer™ can be used to modify the 3D scan for additive or subtractive manufacturing. Optionally, the process can use the rotate and move functionalities to position the stoma and/or surrounding area at the center of the domain. In aspects, unwanted portions of the mesh can be cut off or otherwise removed/excised; for example, the process can use a "knife" tool and hover over a bisect or related tool to select it. Optionally, the number of mesh elements can be reduced or increased.

Figure 12:
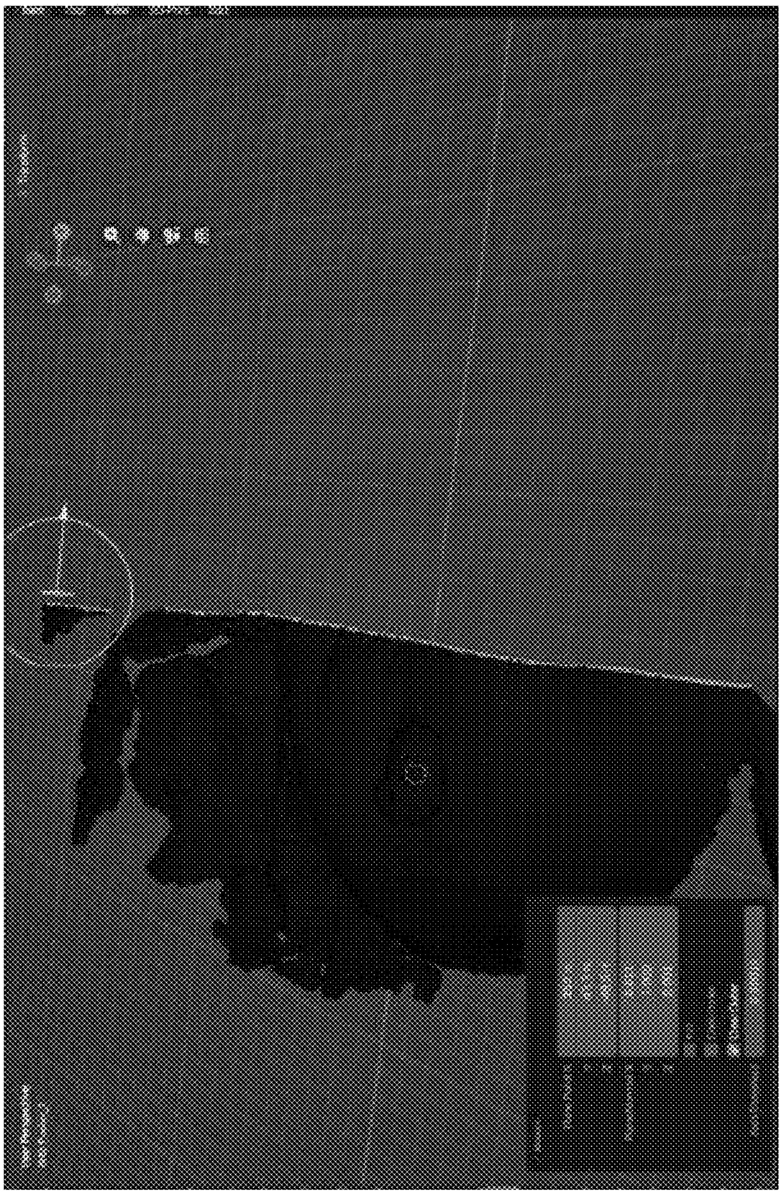
FIG. 12 shows an example of using computer-implemented software to practice aspects of the invention described herein.

As shown in FIG. 12, a user can go from object mode to edit mode and select the mesh. The user can use a knife tool and hover over a bisect tool to select it, then, in aspects, click and drag to cut the mesh, as well as use an angle constraint, expand the bisect tool, select clear inner and/or clear outer regions to remove any unwanted part(s), then repeat the steps to cut out a box around the stoma.

Figure 13:
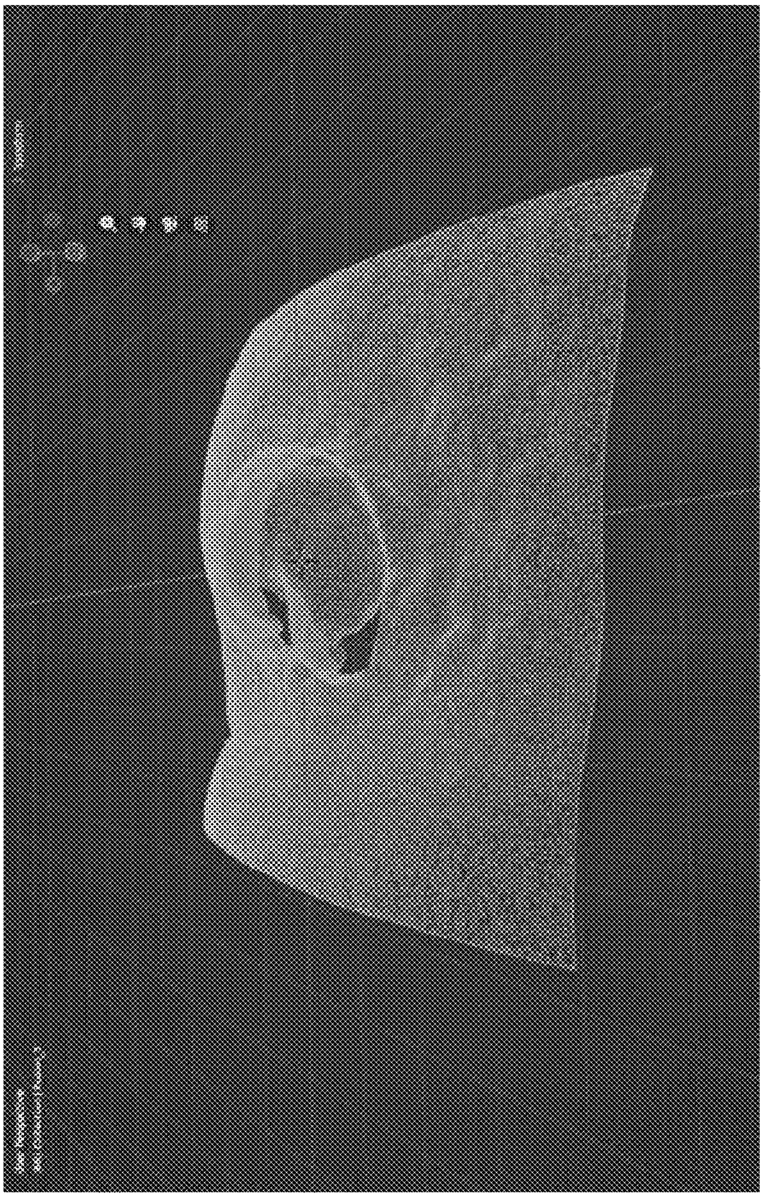
FIG. 13 shows an example of using computer-implemented software to practice aspects of the invention described herein.

As shown in FIG. 13, a user can reduce a number of mesh elements by, in aspects, using a wrench tool and selecting a decimate modifier, and a ratio can be reduced.

Figure 14:
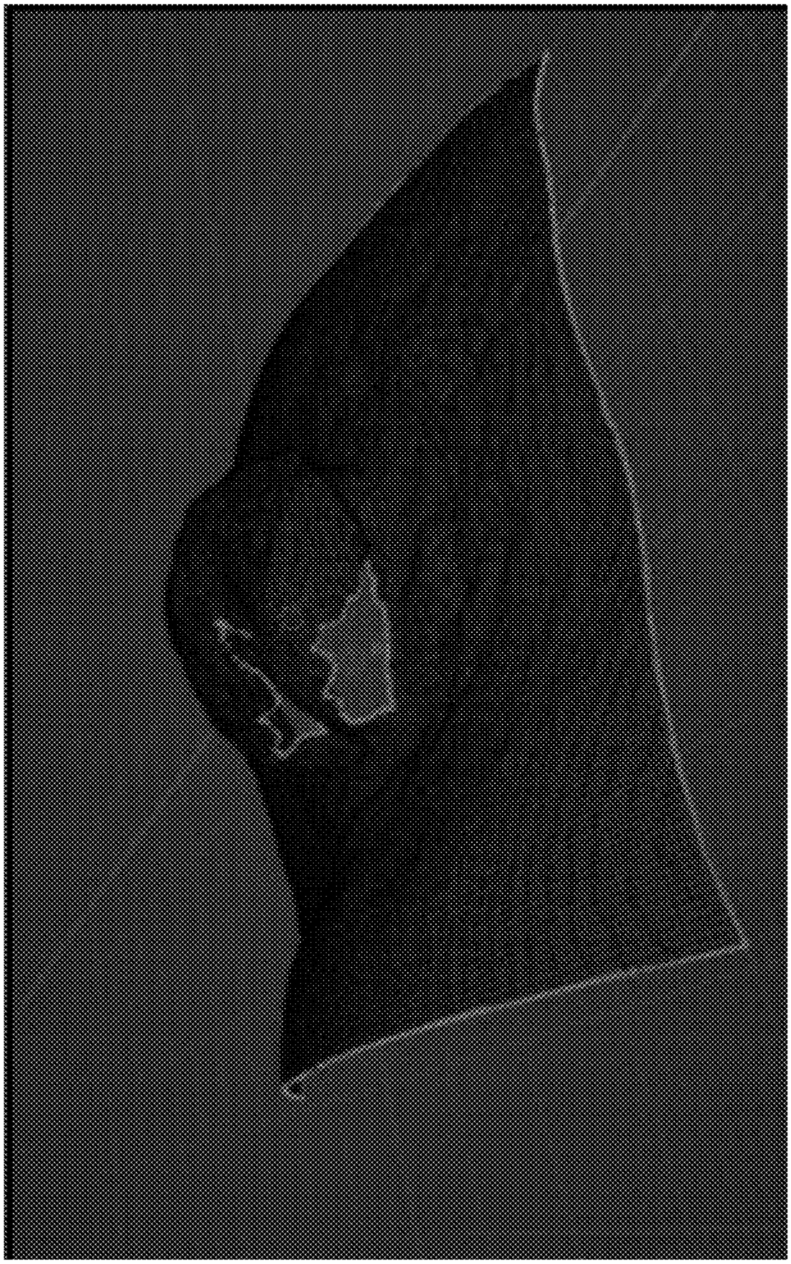
FIG. 14 shows an example of using computer-implemented software to practice aspects of the invention described herein.
Figure 15:
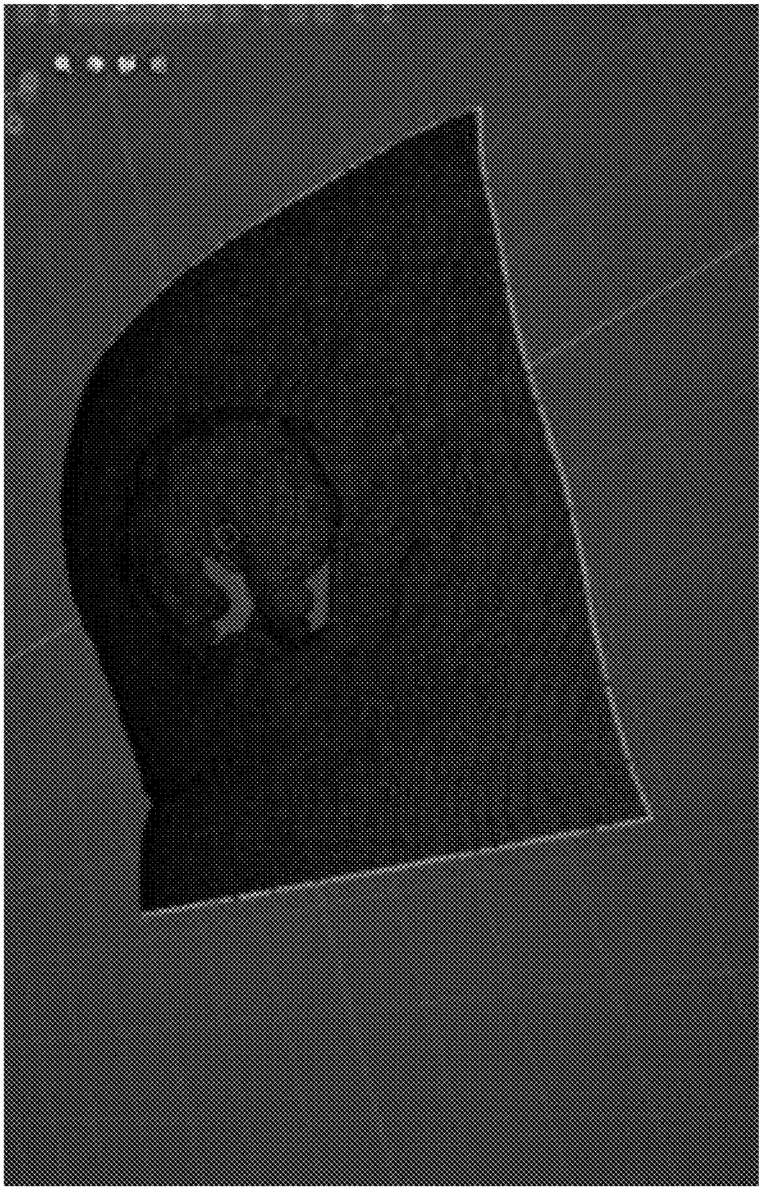
FIG. 15 shows an example of using computer-implemented software to practice aspects of the invention described herein.
Figure 16:
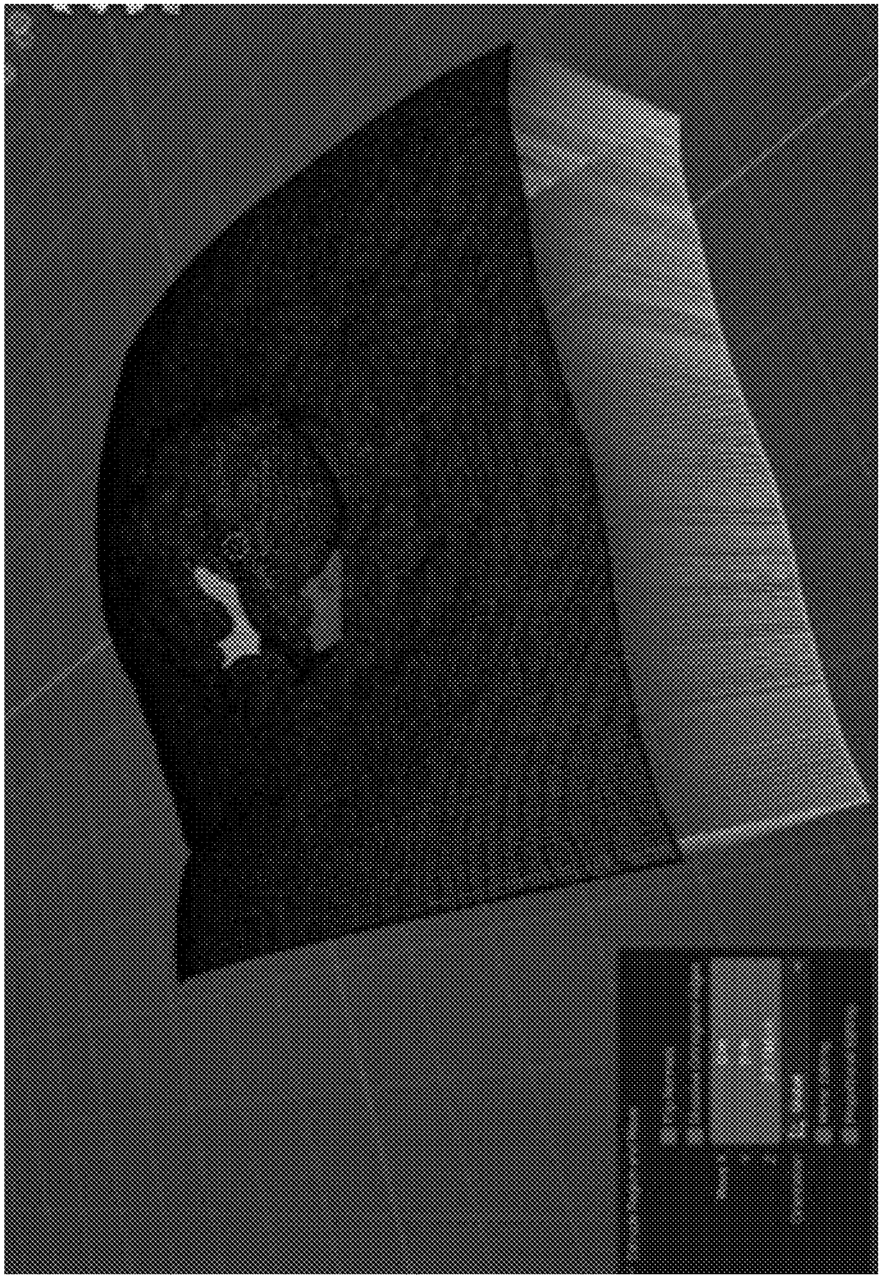
FIG. 16 shows an example of using computer-implemented software to practice aspects of the invention described herein.

As shown in FIGS. 14-16, a user can extrude the mesh to create a base by, in aspects, selecting the mesh, selecting a boundary loop, shading the wireframe, and deselecting any interior boundaries that should not be included in a perimeter loop. A user can enable the 3D printing function and repair any non-manifold mesh. In aspects, a user can add a cylinder to merge with the stoma, and thereby move and scale the cylinder so that, for example, it completely encompasses the stoma. A user can select the stoma and/or cylinder, and delete parts of the mesh that are free floating or seem to be errors in the 3D scan. If there are holes, the mesh can be repaired. In aspects, a user can perform another bisect to make a bottom of the stoma flat and readjust a position and/or size of the cylinder so that the base does not have excess height and/or other problems. Once this is performed a model can be printed using 3D printing and/or additive manufacturing. Any or all aspects can be performed automatically using the computer-implemented method(s) described herein.

In aspects described herein, such as using subtractive manufacturing, by way of example, a user can create an offset plane through where a template or baseplate could be cut using laser subtraction and/or another cutting method, such as using a blade. Alternatively, a user can, for example, create a plane through two, three, or more points by selecting all or a portion around a base.

Figure 17:
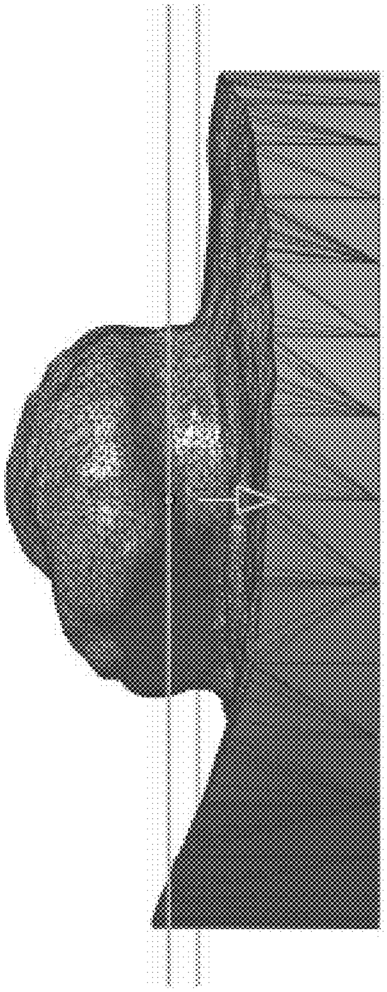
FIG. 17 shows an example of using computer-implemented software to practice aspects of the invention described herein.
Figure 18:
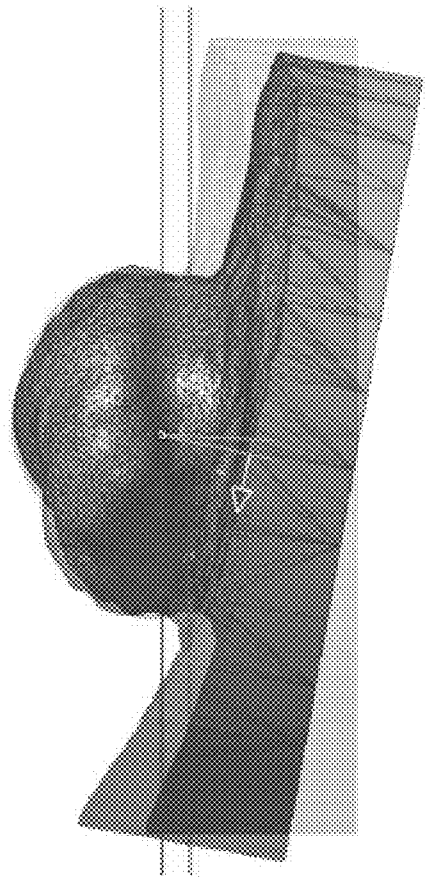
FIG. 18 shows an example of using computer-implemented software to practice aspects of the invention described herein.
Figure 19:
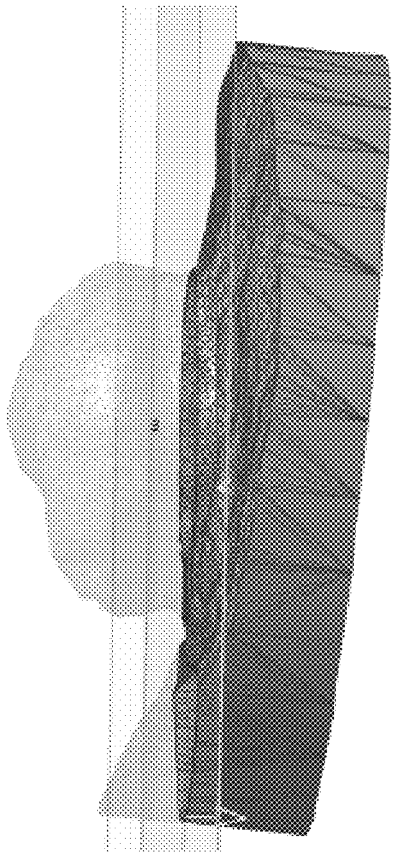
FIG. 19 shows an example of using computer-implemented software to practice aspects of the invention described herein.

For example, as shown in FIGS. 17-19, a stoma mesh or model can be rotated (see, e.g., FIG. 17). As shown in FIGS. 18-19, the model/mesh stoma can be chosen and rotated and aspects of the virtual model can be removed or otherwise manipulated.

Figure 20:
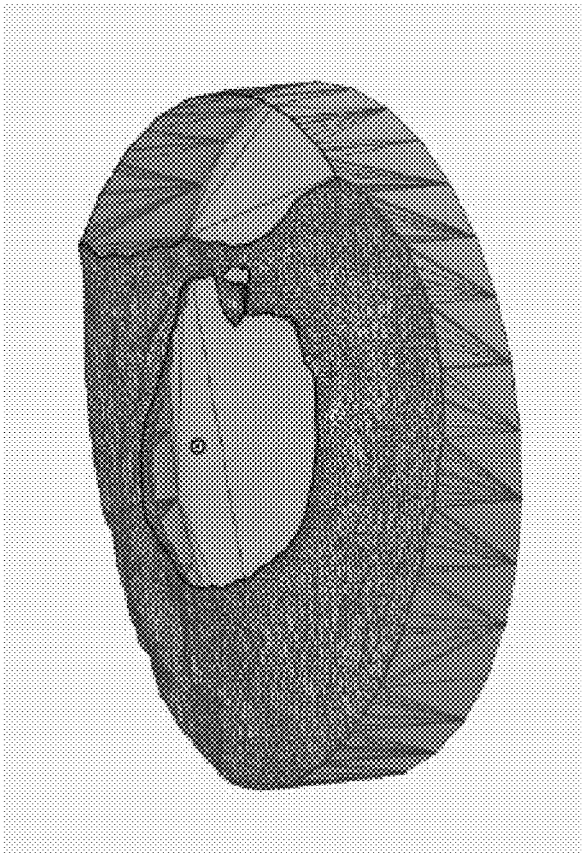
FIG. 20 shows an example of using computer-implemented software to practice aspects of the invention described herein.

As shown in FIG. 20, by way of example, a spline tool can be used to trace an outline of a stoma and an outline can be increased or otherwise grown. This can dictate a file to be read by, for example, a laser cutter, which can be used to laser cut an existing device (e.g., baseplate) for a custom fit on or over a patient's stoma. Alternatively, the contour could be used as a basis for creating a blade holder or press to cut an existing device.

FIGS. 1 through 20 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Further, the present invention encompasses present and future known equivalents to the known components referred to herein by way of illustration.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

The foregoing description of the specific embodiments so fully reveals the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A method for generating a customized ostomy baseplate, the method comprising:

via three-dimensional scanning operations, acquiring a peristomal contour map of a patient;

determining contour map data of a stomal region of the patient based on the peristomal contour map;

generating filtered contour map data by computationally filtering the contour map data in relation to an ostomy baseplate based on the stomal region of the patient;

generating a customized stoma template based on the computationally filtered contour map data; and modifying the ostomy baseplate by applying the customized stoma template thereto, wherein the modifying includes using subtractive manufacturing to match the ostomy baseplate to the customized stoma template, thereby generating the customized ostomy baseplate based on the computationally filtered contour map data.

2. The method of claim 1, wherein the subtractive manufacturing is chosen from one or more of laser cutting, laser subtraction, laser ablation, or a using a blade press.

3. The method of claim 1, wherein generating the customized stoma template includes printing the customized stoma template using a three-dimensional printer.

4. The method of claim 1, further comprising:
informing a shape and/or a design of the customized stoma template based on inputting patient-specified variables chosen from one or more of degree of retraction or protrusion of a stoma or stomal region, a peristomal wound or wounds, and peristomal abdominal wall crease or creases.

5. The method of claim 1, further comprising:
informing a shape and/or a design of the customized stoma template based on inputting patient-specified variables including skin coverage offset.

6. The method of claim 1, further comprising:
informing a shape and/or a design of the customized stoma template based on inputting patient-specified variables including a radial edge offset between a mucocutaneous border.

7. The method of claim 1, further comprising:
informing a shape and/or a design of the customized stoma template based on inputting patient-specified variables including excess height of a patient's ostomy that will not be covered.

8. The method of claim 1, further comprising:
informing a shape and/or a design of the customized stoma template based on inputting patient-specified variables including ostomy grade.

9. The method of claim 1, further comprising:
informing a shape and/or a design of the customized stoma template based on inputting patient-specified variables including a baseplate slope from a maximum height to a peristomal skin surface height.

10. The method of claim 1, further comprising:
informing a shape and/or a design of the customized stoma template based on inputting patient-specified variables including inclusion and exclusion zones.

11. The method of claim 1, further comprising:
informing a shape and/or a design of the customized stoma template based on inputting patient-specified variables including different areas on peristomal skin of the patient.

12. The method of claim 1, further comprising:
informing a shape and/or a design of the customized stoma template based on whether a patient's peristomal skin has an open wound.

13. The method of claim 1, further comprising:
informing a shape and/or a design of the customized stoma template based on whether a patient's peristomal skin is ulcerated.

14. A method for generating a customized ostomy baseplate, the method comprising:
providing an existing ostomy appliance comprising an ostomy baseplate;
via three-dimensional scanning operations, acquiring a peristomal contour map of a patient's stomal region, the peristomal contour map including raw contour map data;
generating filtered contour map data by computationally filtering the raw contour map data;
generating a customized stoma template for fitting the existing ostomy appliance to the patient's stomal region;
generating the customized ostomy baseplate by modifying the ostomy baseplate using the customized stoma template, the modification achieved by applying the customized stoma template to the ostomy baseplate and laser subtracting material from the ostomy baseplate to match a shape and/or a design of the customized stoma template.

15. A method of generating a customized negative pressure vacuum baseplate for wound healing, the method comprising:
via three-dimensional scanning operations, acquiring a contour map of at least part of a patient's wound and surrounding area to generate contour map data;
computationally filtering the contour map data in relation to a negative pressure vacuum baseplate based on the at least part of a patient's wound and surrounding area;
generating a customized negative pressure vacuum template based on the computationally filtered contour map data; and
modifying the negative pressure vacuum baseplate by applying the customized negative pressure vacuum template to the negative pressure vacuum baseplate and using subtractive manufacturing to match the negative pressure vacuum baseplate to the customized negative pressure vacuum template, thereby providing a customized negative pressure vacuum baseplate based on the computationally filtered contour map data.

16. A method of generating a customized fistula management pouch baseplate for wound healing, the method comprising:
via three-dimensional scanning operations, acquiring a contour map of at least part of a patient's fistula and surrounding area to generate contour map data;
computationally filtering the contour map data in relation to a fistula management pouch baseplate based on the at least part of a patient's fistula and surrounding area;
generating a customized fistula management pouch template based on the computationally filtered contour map data; and
modifying the fistula management pouch baseplate by applying the customized fistula management pouch template to the fistula management pouch baseplate and using subtractive manufacturing to match the fistula management pouch baseplate to the customized fistula management pouch template, thereby providing a customized fistula management pouch baseplate based on the computationally filtered contour map data.

* * * * *